(12) United States Patent
Kuhara et al.

(10) Patent No.: US 9,804,246 B2
(45) Date of Patent: Oct. 31, 2017

(54) MAGNETIC RESONANCE IMAGING APPARATUS

(75) Inventors: Shigehide Kuhara, Otawara (JP); Ayako Ninomiya, Tokyo (JP)

(73) Assignee: TOSHIBA MEDICAL SYSTEMS CORPORATION, Otawara-Shi, Tochigi-Ken (JP)

(*) Notice: Subject to any disclaimer, the term of this patent is extended or adjusted under 35 U.S.C. 154(b) by 1272 days.

(21) Appl. No.: 13/010,007

(22) Filed: Jan. 20, 2011

(65) Prior Publication Data

US 2011/0178392 A1 Jul. 21, 2011

(30) Foreign Application Priority Data

Jan. 20, 2010 (JP) ................................ 2010-010412

(51) Int. Cl.
*A61B 5/055* (2006.01)
*G01R 33/565* (2006.01)
*G06T 7/20* (2017.01)
*G01R 33/563* (2006.01)
*G01R 33/567* (2006.01)

(52) U.S. Cl.
CPC ........ *G01R 33/56509* (2013.01); *A61B 5/055* (2013.01); *G01R 33/5635* (2013.01); *G06T 7/20* (2013.01); *G01R 33/5676* (2013.01); *G01R 33/56325* (2013.01); *G06T 2207/10088* (2013.01); *G06T 2207/20016* (2013.01); *G06T 2207/30048* (2013.01)

(58) Field of Classification Search
CPC ............. G01R 33/543; G01R 33/5635; G01R 33/5676; G01R 33/56325; G01R 33/56509; A61B 8/00; A61B 5/055; G06T 2207/10088; G06T 2207/20016; G06T 2207/30048; G06T 7/20
USPC ........ 600/410, 413, 534, 536; 382/106, 107, 382/128, 130, 209, 221, 280, 299
See application file for complete search history.

(56) References Cited

U.S. PATENT DOCUMENTS

| 6,359,630 B1 * | 3/2002 | Morse et al. ................. 345/620 |
| 2006/0241511 A1 * | 10/2006 | Warmuth ............. A61B 5/0456 600/536 |
| 2008/0187180 A1 | 8/2008 | Yui |

FOREIGN PATENT DOCUMENTS

| JP | 2008-302214 | 12/2008 |
| JP | 2009-178264 | 8/2009 |

* cited by examiner

*Primary Examiner* — Ruth S Smith
(74) *Attorney, Agent, or Firm* — Nixon & Vanderhye P.C.

(57) ABSTRACT

According to one embodiment, an image processing apparatus includes a storage unit configured to store data of a series of slice images associated with a region including a target region of an object, a first rest period specifying unit configured to specify a first rest period based on a change between images of the series of slice images, and a second rest period specifying unit configured to specify a second rest period shorter than the first rest period by tracking the target region on a plurality of slice images corresponding to the specified first rest period or a rest period enlarged from the first rest period.

18 Claims, 10 Drawing Sheets

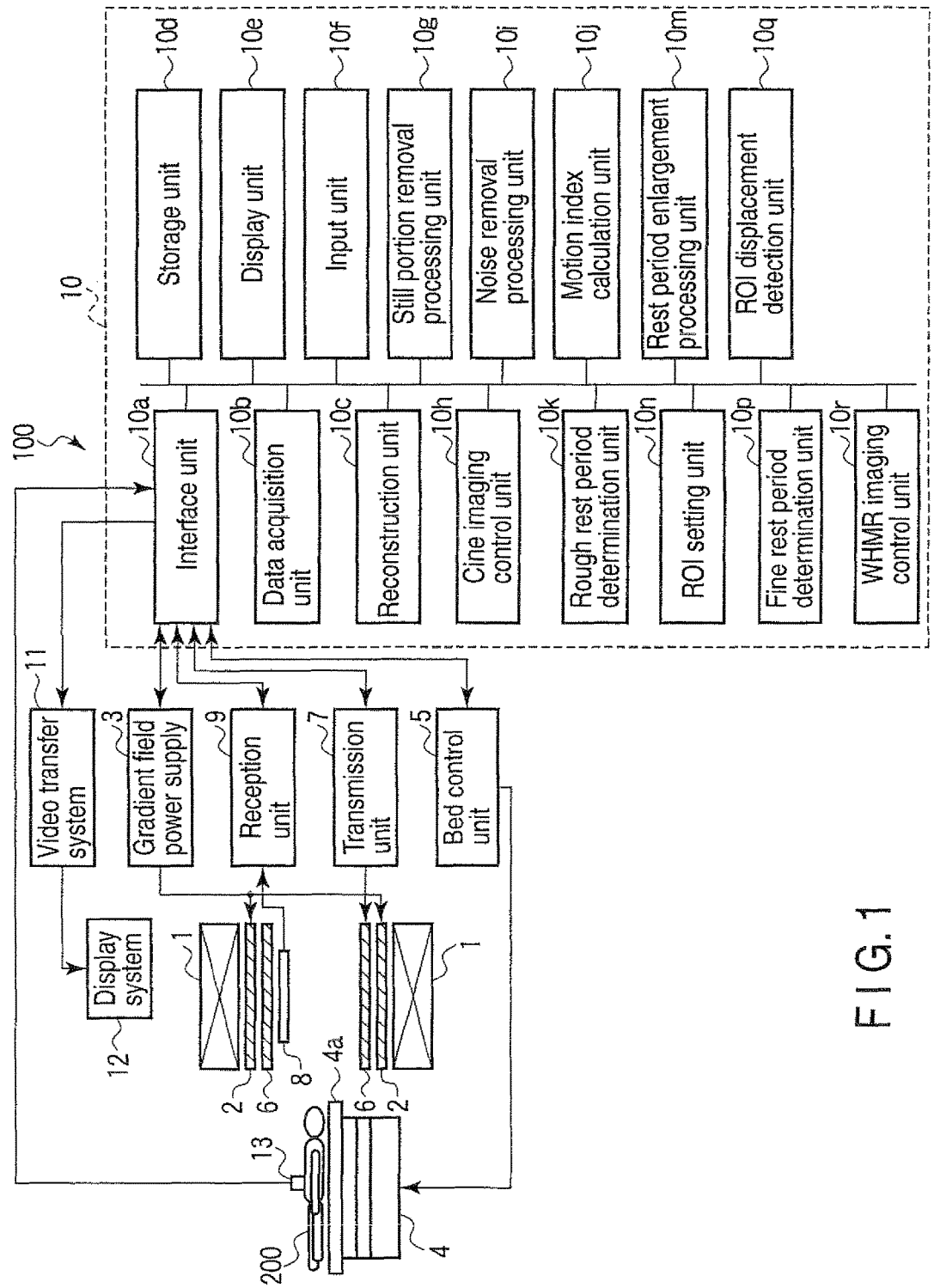
F I G. 1

MAGNETIC RESONANCE IMAGING APPARATUS

CROSS-REFERENCE TO RELATED APPLICATIONS

This application is based upon and claims the benefit of priority from Japanese Patent Application No. 2010-010412, filed Jan. 20, 2010; the entire contents of which are incorporated herein by reference.

FIELD

Embodiments described herein relate generally to a magnetic resonance imaging apparatus.

BACKGROUND

When a magnetic resonance imaging apparatus (MRI) captures an image of coronary arteries, in particular an image of the coronary artery distribution of the whole heart (Whole Heart MRCA), the apparatus uses method of imaging under natural aspiration using a three-dimensional ssfp sequence. At this time, the apparatus performs imaging while correcting the movement of the heart due to respiratory movement by using the RMC (Real-time Motion Correction) method. With regard to cardiac pulsation, the time from an R-wave to an imaging timing is adjusted by ECG gating using an electrocardiograph (ECG) so as to perform data acquisition in a rest period during which the coronary arteries are relatively at rest.

Conventionally, the operator sees cine images captured in advance to determine a period during which the coronary arteries are at rest, and performs actual imaging in the determined period. For this reason, it takes much time to set a rest period of the coronary arteries. Furthermore, the reliability of the set rest period depends on the skill of the doctor.

BRIEF DESCRIPTION OF THE DRAWINGS

FIG. 1 is a block diagram showing the arrangement of a magnetic resonance imaging apparatus according to an embodiment of the present invention;

Figure 2:
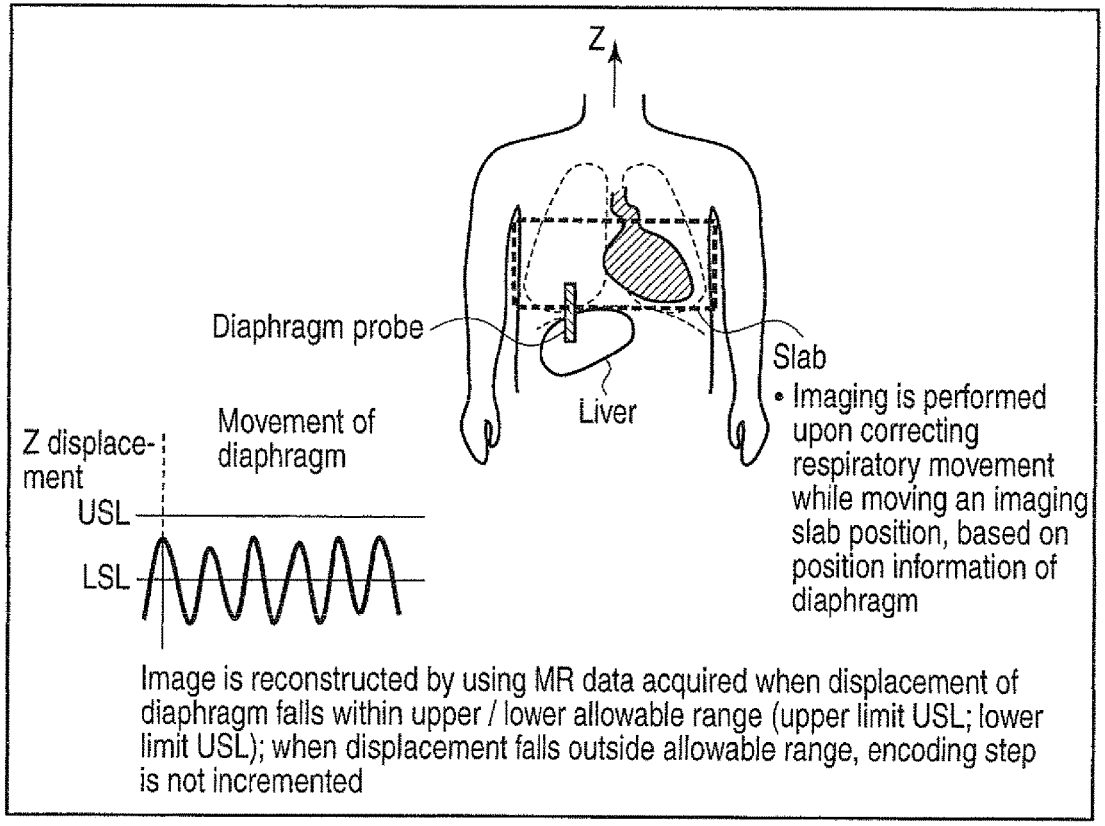
FIG. 2 is a view for explaining actual scanning (RMC (Real-time Motion Correction)) in this embodiment.

DETAILED DESCRIPTION general, according to one embodiment, a magnetic resonance imaging apparatus repeats an imaging scan on an overall heart of an object, detects the displacement of the diaphragm due to the respiratory movement of the object by executing a probe scan immediately before each of the imaging scans, and displaces an imaging range for each of the imaging scans based on the detected displacement of the diaphragm. A control unit controls an RF coil reception/transmission unit and a gradient field power supply to generate a series of slice images by repeatedly imaging a region including the heart by ECG gating for preliminary scans for the probe scans and the imaging scans. This apparatus specifies, for the series of slice images, the first rest period in which a variation in position of the coronary artery falls within a predetermined range in a cardiac cycle, based on a change in the image of the overall heart. The apparatus specifies the second rest period of the coronary artery in the cardiac cycle, for a plurality of slice images, of the series of slice images, which correspond to the specified first rest period or a rest period enlarged from the first rest period, by tracking the movement of the coronary artery only within a local range including the coronary artery. The apparatus then reconstructs an image based on MR data acquired in the second rest period.

An embodiment of the present invention will be described below with reference to the views of the accompanying drawing.

FIG. 1 shows the arrangement of a magnetic resonance imaging apparatus (MRI apparatus) according to this embodiment. An MRI apparatus 100 includes a static field magnet 1. The static field magnet 1 typically has a hollow cylindrical shape. The static field magnet 1 generates a uniform static field in the cylindrical portion. The static field magnet 1 is formed by a permanent magnet or superconductive magnet.

A gradient field coil unit 2 is placed inside the static field magnet 1. The gradient field coil unit 2 includes three types of coils, i.e., X-, Y-, and Z-axis coils, respectively corresponding to the orthogonal X-, Y-, and Z-axes. The X- and Y-axes are respectively defined in the horizontal and vertical directions. In general, the Z-axis is located on the cylindrical centerline. An object is inserted into the cylindrical space so as to make his/her body axis almost coincide with the Z-axis. The three types of coils respectively receive currents supplied from a gradient field power supply 3 and generate gradient fields which change along the X-, Y-, and X-axes. Note that a static field is formed parallel to the Z-axis. Typically, the gradient fields along the X-, Y-, and Z-axes are respectively used as a slice selecting gradient field Gs, a phase encoding gradient field Ge, and a readout gradient field Gr.

A bed 4 includes a top 4a movable in the Z-axis direction. The longitudinal direction of the top 4a is parallel to the Z-axis. An object 200 is inserted into the cylindrical space of the gradient field coil unit 2 while being placed on the top 4a. A bed control unit 5 controls the movement of the top 4a. An electrocardiograph (ECG) 13 is attached to the object 200.

A transmission RF coil 6 is placed inside the gradient field coil unit 2. The transmission RE coil 6 receives high-frequency pulses from a transmission unit 7 and generates a high-frequency magnetic field. The transmission unit 7 transmits high-frequency pulses corresponding to the Larmor frequency to the transmission RF coil 6. A reception RF coil 8 is placed inside the gradient field coil unit 2. A reception unit 9 receives, via the reception RF coil 8, NMR signals generated in the relaxation process of magnetized spins excited by a high-frequency magnetic field. The reception RF coil 8 may also serve as the transmission RF coil 6.

A computer system 10 is connected to the gradient field power supply 3, the bed control unit 5, the transmission unit 7, the reception unit 9, and the ECG 13 via an interface unit 10*a*. A data acquisition unit 10*b* acquires the digital signals output from the reception unit 9 via the interface unit 10*a*. The data acquisition unit 10*b* stores the acquired digital signal, i.e., the NMR signal data, in a storage unit 10*d*. A reconstruction unit 10*c* reconstructs the spectrum data or image data of nuclear spins by reconstruction processing such as Fourier transformation based on the NMR signal data stored in the storage unit 10*d*. The storage unit 10*d* stores NMR signal data and spectrum data or age data for each object.

A display unit 10*e* is provided to display various kinds of information such as spectrum data and image data. An input unit 10*f* is provided to allow the operator to input various kinds of commands and information to the computer system 10. It is possible to use, as the input unit 10*f*, pointing devices such as a mouse and a trackball, selection devices such as a mode switch, and input devices such as a keyboard, as needed.

Figure 3:
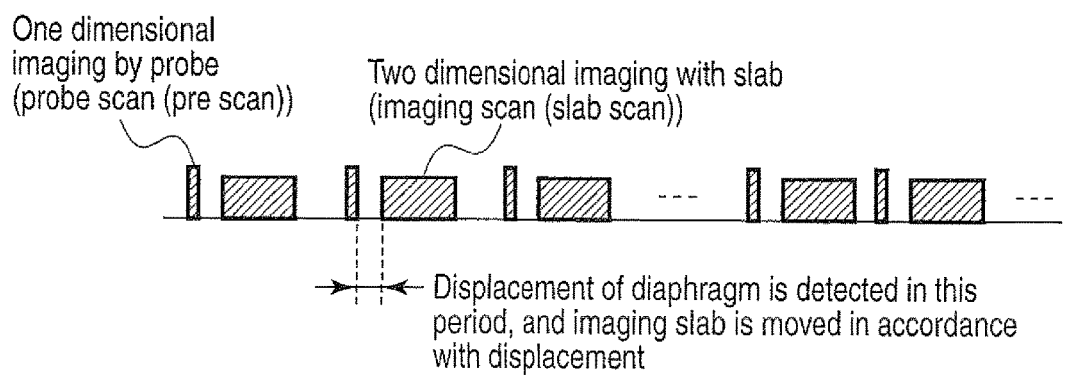
FIG. 3 is a view for explaining actual scanning in this embodiment.

In this case, this embodiment causes a WHMR imaging control unit 10*r* to control the transmission and reception units 7 and 9 for the RF coils 6 and 8 and the gradient field power supply 3 to capture an image of the coronary arteries of the object, which moves due to respiratory movement and pulsation of the object, by using a technique called RMC (Real-time Motion Correction). This image capturing will be referred to as main scanning. As shown in FIGS. 2 and 3, in main scanning, this apparatus repeats an imaging scan (slab scan) accompanying phase-encoding increment using a two- or three-dimensional Fourier transform method. This will repeat the acquisition of MR data with different phase encoding values. The apparatus reconstructs an image from MR data sets throughout all the phase encoding values. In main scanning, immediately before each imaging scan, the apparatus executes a probe scan (navigator scan) for detecting the moving distance, i.e., the displacement, of the diaphragm, which moves due to the respiratory movement of the object, from a reference position (the position in the first scan). The apparatus then displaces the imaging range (excitation range which is also called a slab) aiming at the overall heart by an imaging scan based on the displacement of the diaphragm which is detected by the probe scan.

That is, in RMC, the displacement of the heart is estimated based on the displacement of the diaphragm. If there are differences between the displacements of the diaphragm and the displacements of the heart, in particular the displacements of the diaphragm and the fine motions of the coronary arteries, the data acquisition position changes within an MR data set. This produces artifacts in an image. Although the apparatus acquires MR data used for reconstruction by repeating an imaging scan while changing the phase encoding step, it is important, from the viewpoint of reducing motion artifacts, to make the coronary arteries be relatively still in an MR data set, i.e., to make variations in the positions of the coronary arteries fall within a predetermined range.

This apparatus basically uses a set of slice images (cine images) repeatedly captured at an imaging plane in which the left and right coronary arteries are included in the same slice, for example, a slice traversing the heart (a slice perpendicular to oblique to the cardiac axis connecting the apex and the base of the heart), e.g., a four-chamber slice or two-chamber slice, as basic data specifying a rest period of the coronary arteries. Note that a rest period of the coronary arteries is not limited to a period during which the coronary arteries exist at the same position in a strict sense but is defined as a period during which the displacements of the coronary arteries fall within a given range in which it is possible to reduce motion artifacts to the extent that they have little influence on diagnosis.

This apparatus obtains a rest period of the coronary arteries as follows. First of all, the apparatus compares each adjacent pair of these slice images to obtain the differences between the images or correlation coefficients, thereby obtaining motion indices. When the heart and the coronary arteries are almost at rest, the difference between adjacent images decreases. For example, according to the difference method, it is possible to specify, as a rest period, a period corresponding to the total sum of residual pixels after difference calculation between images (residual pixel count) which is equal to or less than a threshold near 0. According to the crosscorrelation method, if there is no difference between images, the correlation coefficient approximates to 1.0. It is therefore possible to specify, as a rest period, a period corresponding to a correlation coefficient which is equal to or more than a threshold approximate to 1.0.

As described above, motion detection methods include methods using the difference method and the crosscorrelation method. The difference method is simple and allows fast calculation but is susceptible to noise. The crosscorrelation method is slightly more robust to noise than the difference method but requires a very large amount of calculation and takes much time if, for example, a calculation region is an entire image.

Motion detection methods are roughly classified into two methods, namely a global method using signals (information) concerning the entire heart and a local method of detecting a motion in a local ROI in a coronary artery portion. The merits of the global method are as follows: it is possible to detect rest phases in the entire region; it is possible to implement full automation (no ROI required); the amount of calculation is large (particularly in the case of crosscorrelation) because of calculation for the entire heart; and there is no need to perform postprocessing associated with the rest times of the left and right coronary arteries because the method is configured to find rest phases in the heart as a whole. The demerits of the global method are that the detection sensitivity is low when the signal change amount of a moving portion is small relative to the signal of a still portion, and a blood flow or the like is likely to be erroneously recognized as a motion, even when the heart is at rest, if there is a change in luminance, that is, the method is susceptible to noise in a broad sense.

The following method of automatically extracting only a moving portion such as the heart is an improved method against one of the problems of the global method, that is, the motion detection sensitivity deteriorates when there is a strong signal based on a still portion. Moving portions and still portions are separated from a series of slice images based on a temporal change of each pixel. Concrete examples of this operation include a method using Fourier transformation and a method using a statistical technique using the spatial distribution of pixel changes. The method using Fourier transformation is configured to separate a moving portion from a still portion based on the phenomenon that when the temporal changes in the pixel values of the respective pixels are Fourier-transformed, a moving portion exhibits a relatively high frequency component, and a still portion exhibits a low frequency component near zero frequency. The statistical method is based on the assumption that a portion exhibiting a large signal change in the time direction is moving, and a place exhibiting a little signal change in the time direction is a still portion. This method therefore separates a moving portion from a still portion by using a statistical technique, for example, discriminant analysis. First of all, the signal of a still portion is removed by this method to leave only a heart portion so as to improve the motion detection sensitivity. The obtained motion temporal changes are then presented. A rest period is extracted from the temporal changes. As described above, if the difference method is used as this method, a rest period is a period during which the residual pixel count decreases lower than a given threshold, and a portion exhibiting little temporal changes continues.

The local method sets a local ROI including a coronary artery portion and tracks the coronary artery portion by using the ROI as a visual field, thereby detecting the displacement of each coronary artery. In tracking a coronary artery portion by using an ROI, for example, this method sets a predetermined search range in a frame, centered on the position of an ROI in the previous frame, and calculates, for example, correlation coefficients between an image portion in the ROI in the previous frame and an image portion in the ROI in the next frame while moving the ROI in the search range. The method then identifies the position of the ROI in the next frame which exhibits the highest correlation coefficient as the position of the coronary artery on the corresponding image. The merits of this local method are, for example, that it is possible to accurately detect motions, and the calculation speed is high. On the other hand, the demerits of the method are, for example, that it is necessary to perform operation to set an ROI, it is not possible to determine the overall motion because detection is separately performed on the left and right sides, and it is difficult to extract rest periods throughout the entire region because the deformation of the coronary arteries will lead to template mismatching.

As described above, it is difficult to simultaneously extract rest periods of the coronary arteries with ease, high accuracy, and high robustness by singly using the global method or the local method.

In order to solve this problem, in this embodiment, first of all, the global method is used to roughly obtain rest periods throughout an entire cardiac cycle, practically a rest period in a systolic phase and a rest period in a diastolic phase. The local method is then applied to only periods narrowed down based on the rough rest periods obtained by the global method. In this manner, this embodiment uses both the global method and the local method.

This embodiment will be specifically described below.

Figure 4:
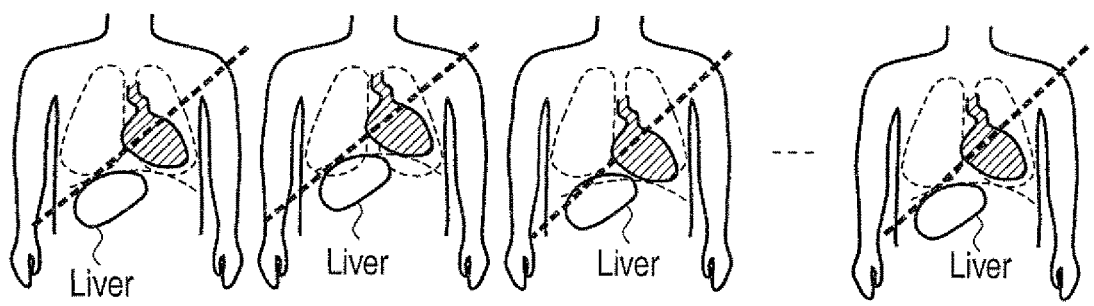
FIG. 4 is a view for explaining preliminary scanning cine imaging) in this embodiment.

In this embodiment, the apparatus specifies a period (rest period) during which the coronary arteries are relatively at rest to the extent that no serious motion artifacts are produced before execution of a main scan (a probe scan and an imaging scan). The embodiment performs a preliminary scan under the control of a cine imaging control unit 10*h* before a main scan, and as shown in FIG. 4, repeatedly acquires slice images associated with slices traversing both the left and right coronary arteries of the heart. The cine imaging control unit 10*h* controls the transmission unit 7, the reception unit 9, and the gradient field power supply 3 to repeatedly capture slice images associated with slices traversing the heart of the object, and stores the mages in the storage unit 10*d*. A preliminary scan uses the ssfp (steady state free precession) imaging method which applies gradient fields in directions opposite to those of the gradient fields Ge, Gs, and Gr so as to match transverse magnetization phases for each of repetitive excitations. An imaging scan for a slice image is repeated for about 1 min under natural aspiration.

Figure 5:
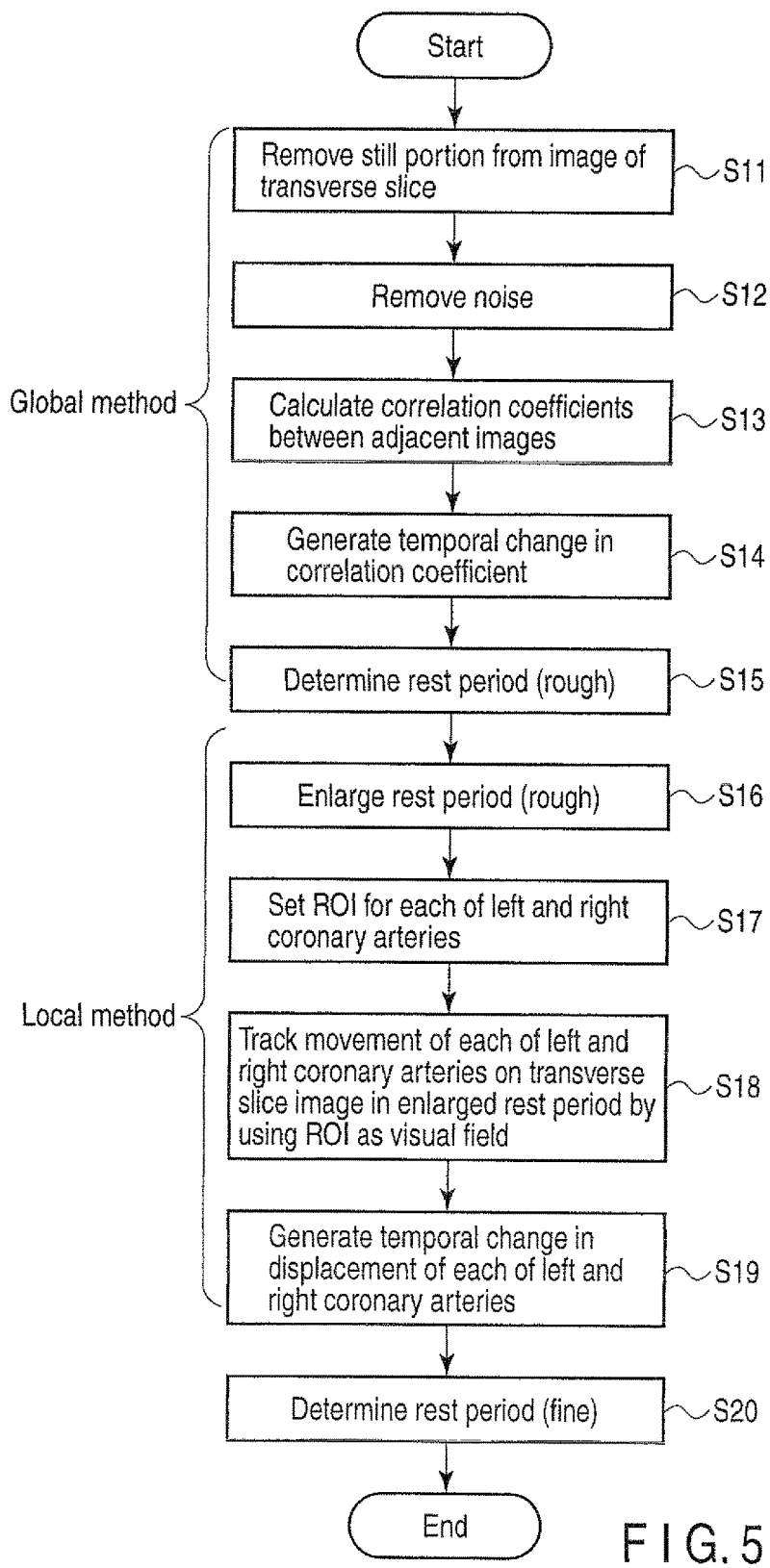
FIG. 5 is a flowchart showing a procedure for specifying a coronary artery rest period in this embodiment.
Figure 6:
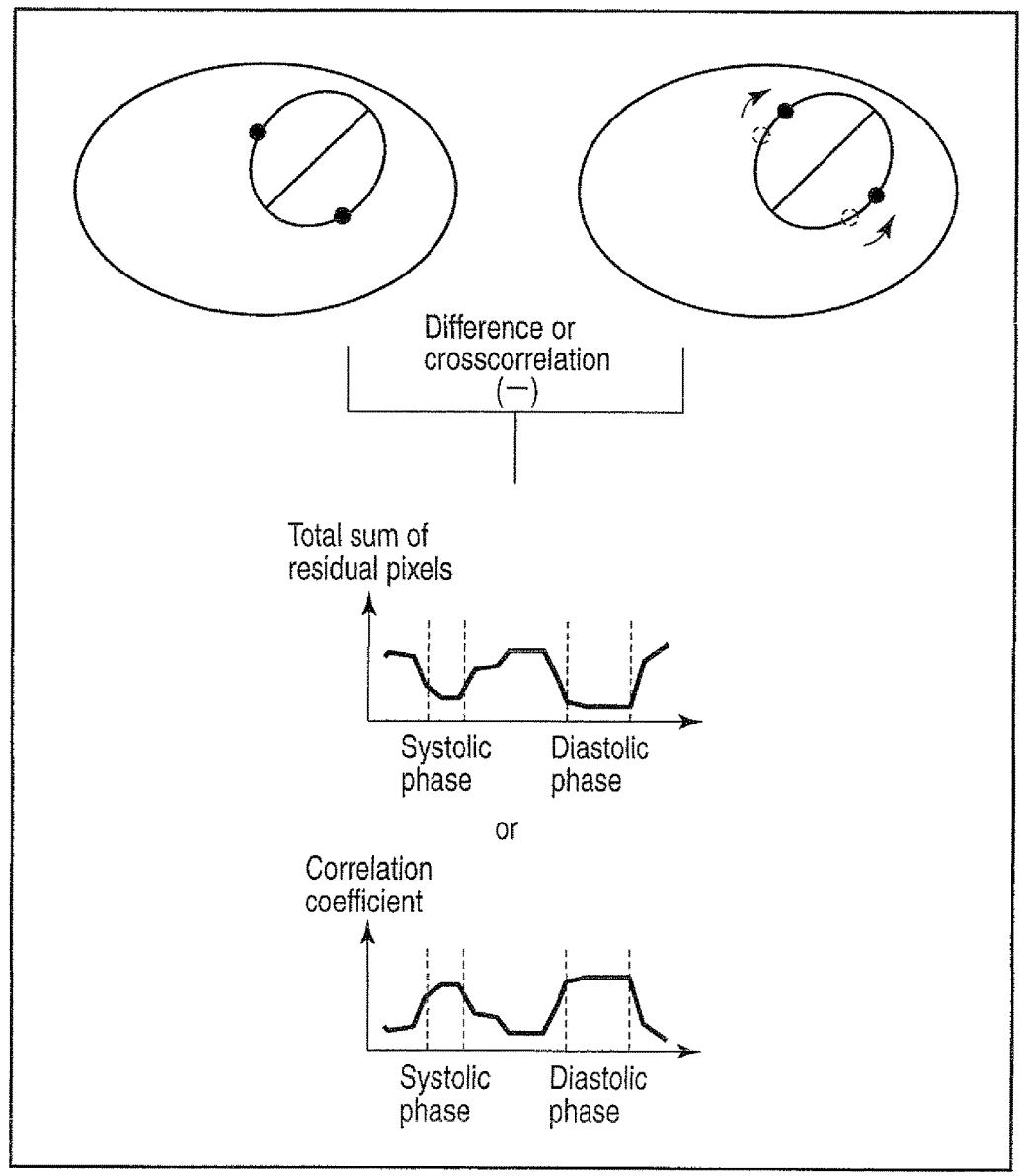
FIG. 6 is a view for explaining an outline of a global method in FIG. 5.
Figure 12:
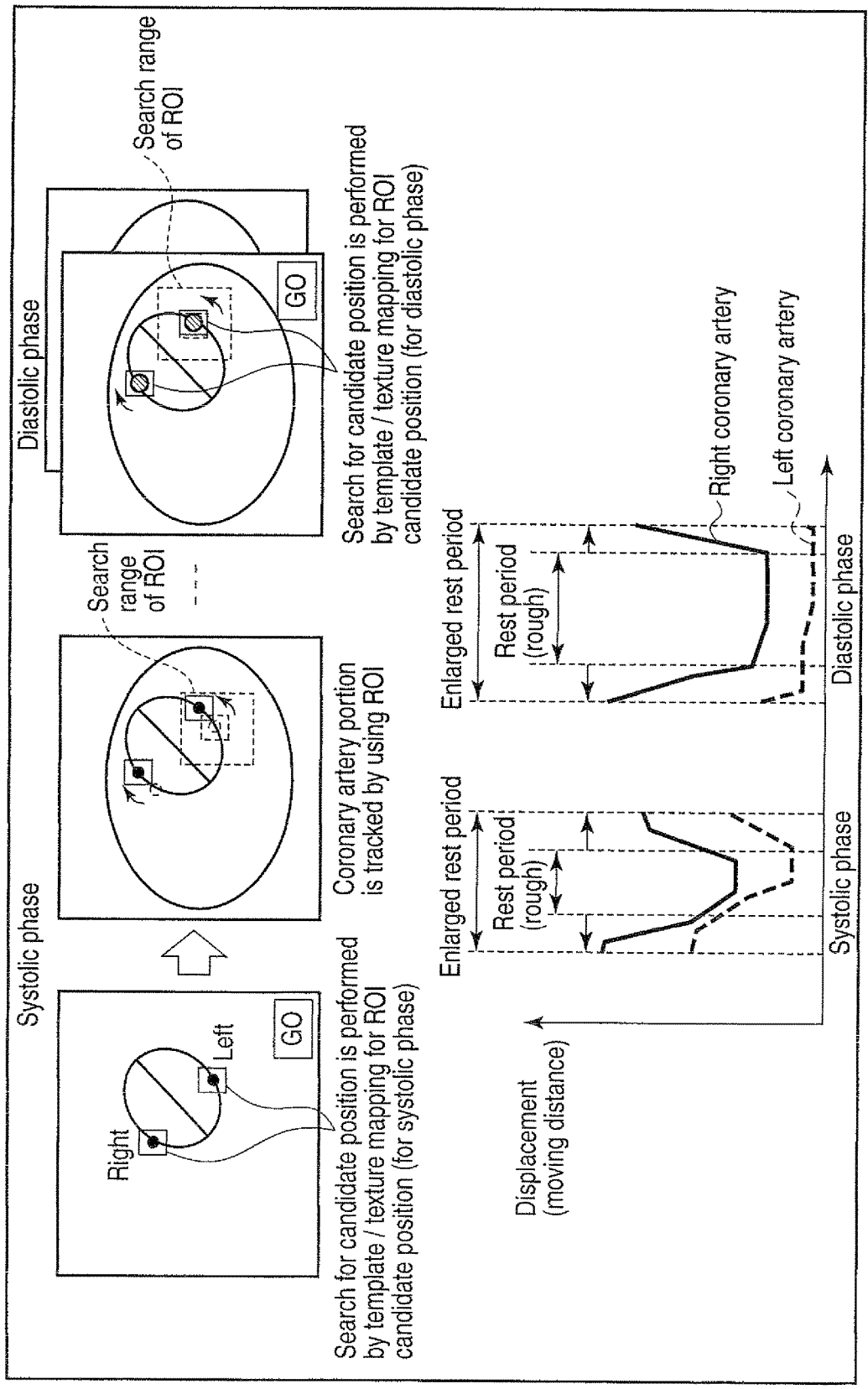
FIG. 12 is a view for explaining rest period enlargement step S16 and ROI setting step S17 in FIG. 5.
Figure 13:
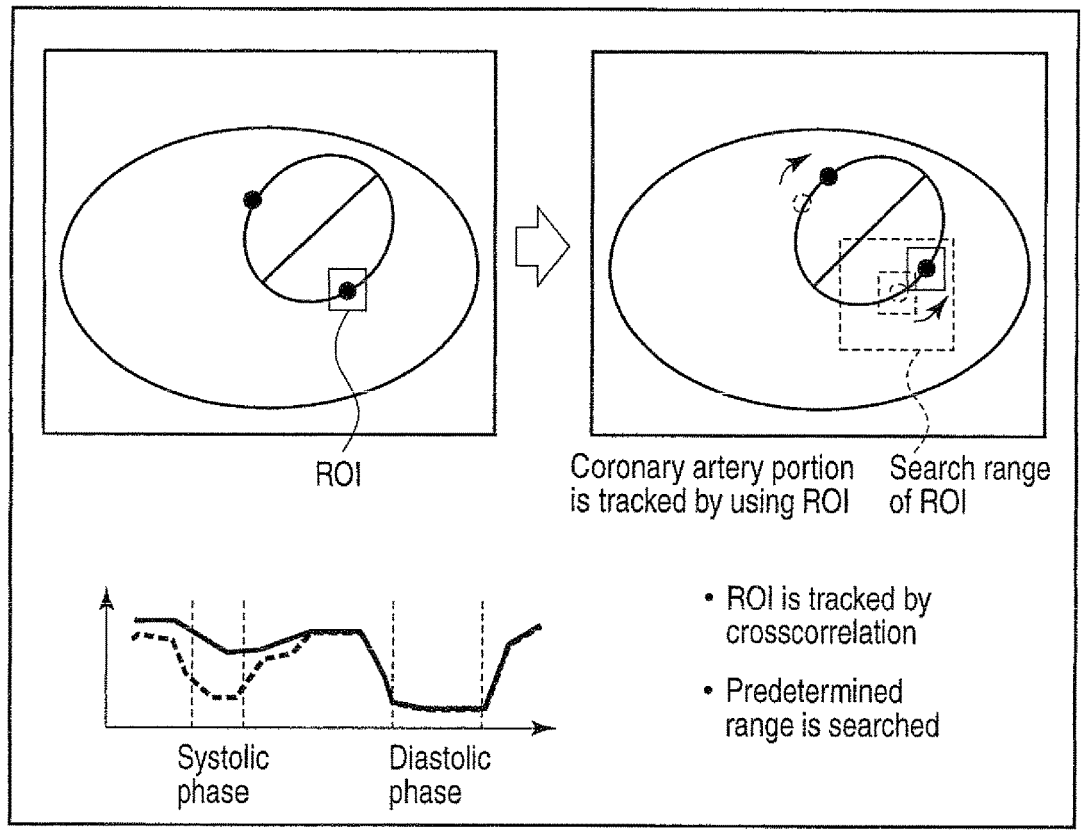
FIG. 13 is a view for explaining tracking step S18 and temporal change generation step S19 in FIG. 5.

This apparatus specifies a rest period of the coronary arteries by using a series of slice images captured by the preliminary scans. FIG. 5 shows a procedure for a rest period specifying process for the coronary arteries. The procedure comprises steps S11-S20. Steps S11-S15 illustrate the global method, and steps S16-S19 illustrate the local method. Steps S1, S12. S13, S14 and S15 includes removing a still portion from the image of transverse slice, removing noise, calculating correlation coefficients between adjacent images, generating temporal change in correlation coefficient, and determining a rough rest period, respectively. Steps S16, S17, S18 and S19, include enlarging the rough rest period, setting the ROI for each of left and right coronary arteries, tracking movement of each of left and right coronary arteries on transverse slice image in enlarged rest period by using ROI as visual field, and generating temporal change in displacement of each of left and right coronary arteries, respectively. After step S19 it is now possible to more finely determine the rest period at step S20. It is important for this embodiment to use both the global method and the local method, as described above. As shown in FIG. 6, the global method roughly specifies a rest period (to be referred to as the first rest period) during which a variation of the coronary artery in a cardiac cycle falls within a predetermined range, based on an index (motion index) indicating the degree of variation in the position of the overall heart by using repeatedly captured slice images. A typical motion index indicating the degree of variation in the position of the overall heart is a temporal change associated with the total sum of residual pixels after the calculation of the differences between adjacent slice images or a temporal change associated with the correlation coefficient calculated between adjacent slice images. As shown in FIGS. 12 and 13, the local method finely (accurately) specifies a rest period (second rest period), during which the coronary artery is relatively at rest in a cardiac cycle, by tracking the movement of the coronary artery only within a local range (ROI) including the coronary artery.

When using both the global method and the local method, this embodiment uses the local method, upon limiting a period corresponding a rest period (first rest period) roughly specified by the global method, to track the movement of the coronary artery on some slice images generated in the period by using an ROI.

Figure 7:
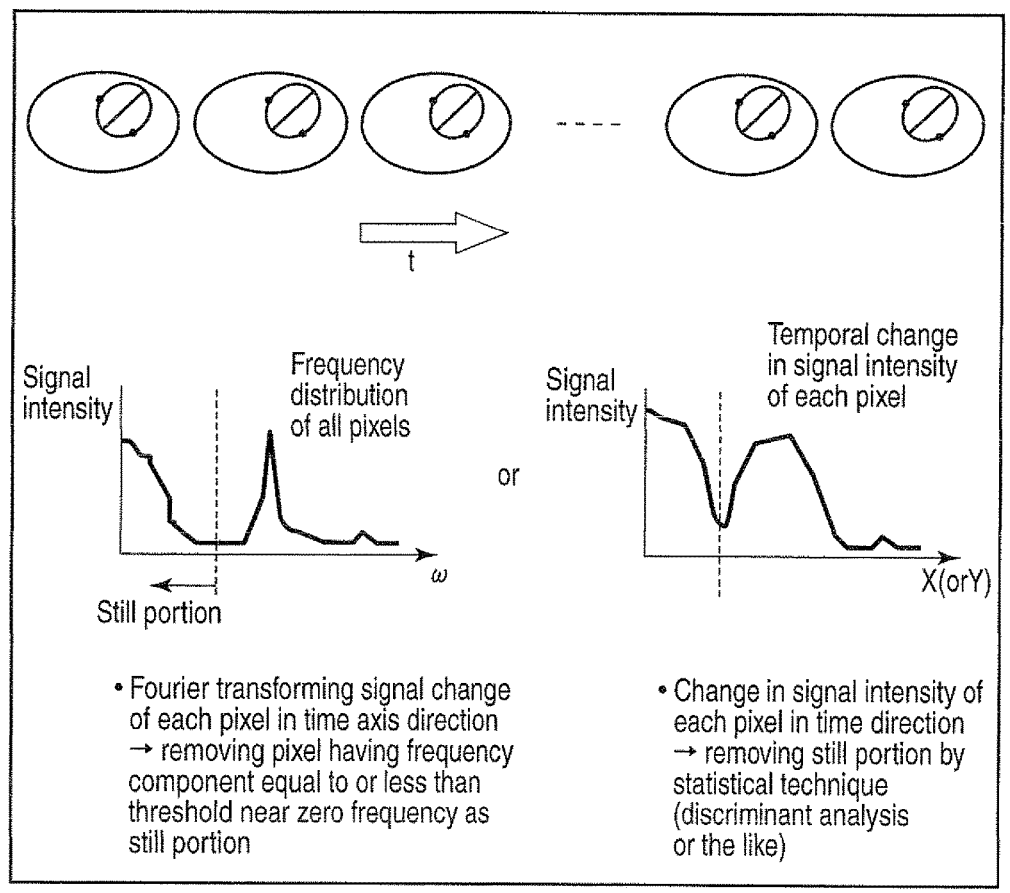
FIG. 7 is a view for explaining still portion removing step S11 in FIG. 5.

First of all, when applying the global method, this embodiment performs removal of still portions, other than the heart, e.g., the thoracic cage as preprocessing. As shown in FIG. 7, a still portion removal processing unit 10*g* generates the time curve (temporal changes) of the signal intensity (pixel value) of each pixel with respect to all the slice images acquired by preliminary scanning, and Fourier-transforms the temporal change of each pixel in the time axis direction. This apparatus removes, from each slice image, pixels exhibiting frequency components equal to or less than a threshold approximate to zero frequency as a result of the Fourier transformation, as pixels in a region corresponding to a still portion such as the thoracic cage, as indicated by the dotted line in FIG. 8. A region of the heart including the coronary arteries exhibits relatively active motions due to the pulsation of the heart, and hence is not removed and remains. There is available another method of calculating the difference between the maximum signal intensity (maximum pixel value) and the minimum signal intensity (minimum pixel value) for each pixel for a predetermined period (cine imaging period), generating the spatial distribution of the differences, and removing a still portion as one block estimated by a statistical technique from the spatial distribution. A noise removal processing unit 10*i* then removes spatially high-frequency noise generated due to the removal of the still portion.

Figure 8:
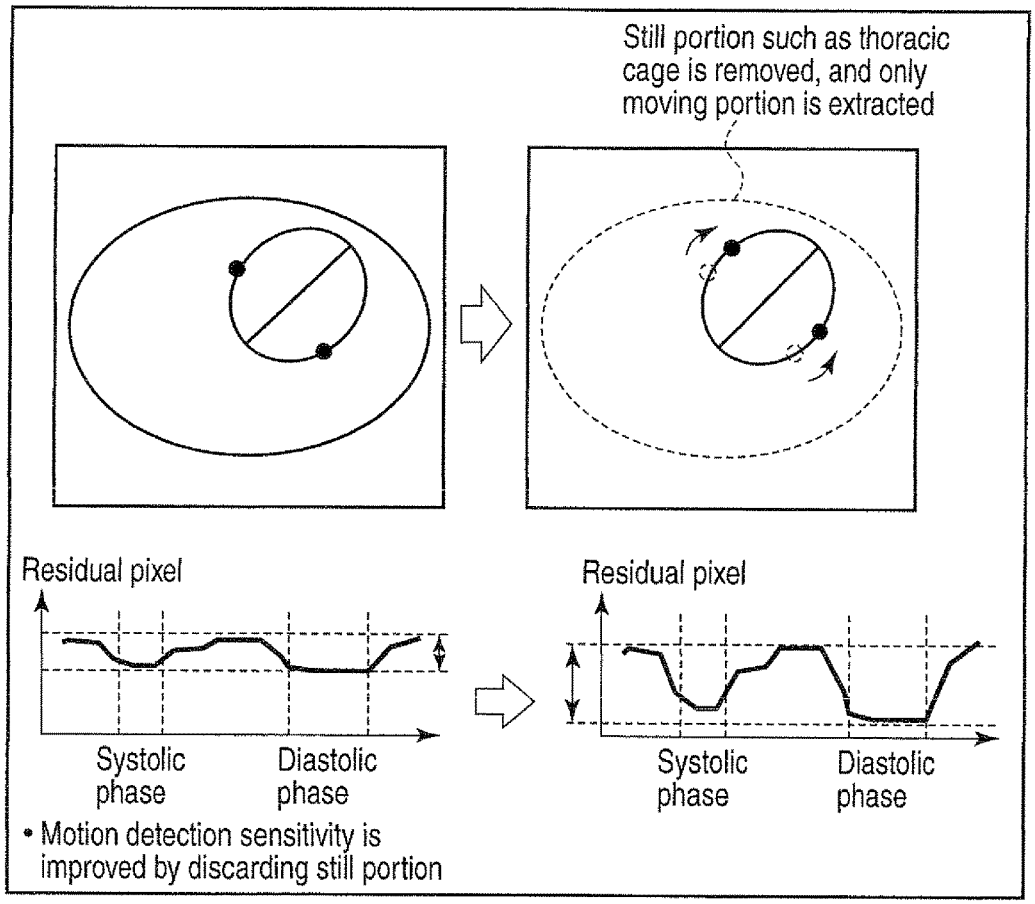
FIG. 8 is a view showing the effect of still portion removing step S11 in FIG. 5.

The global method is then executed to specify the rough first rest period of the coronary arteries. A motion index calculation unit 10*j* calculates a motion index indicating the degree of variation in the position of the overall heart on a slice image from which a still portion is removed (S13). As shown in FIG. 6, a typical example of this motion index is a temporal change (time curve) associated with the total sum of residual pixels after the calculation of the difference between adjacent slice images or a temporal change associated with the correlation coefficient calculated between adjacent slice images. Removing a still portion by preprocessing and extracting a moving portion can very notably express the motions of the overall heart and coronary arteries on the temporal change curve of difference values or correlation coefficients, as shown in FIG. 8.

Figure 10:
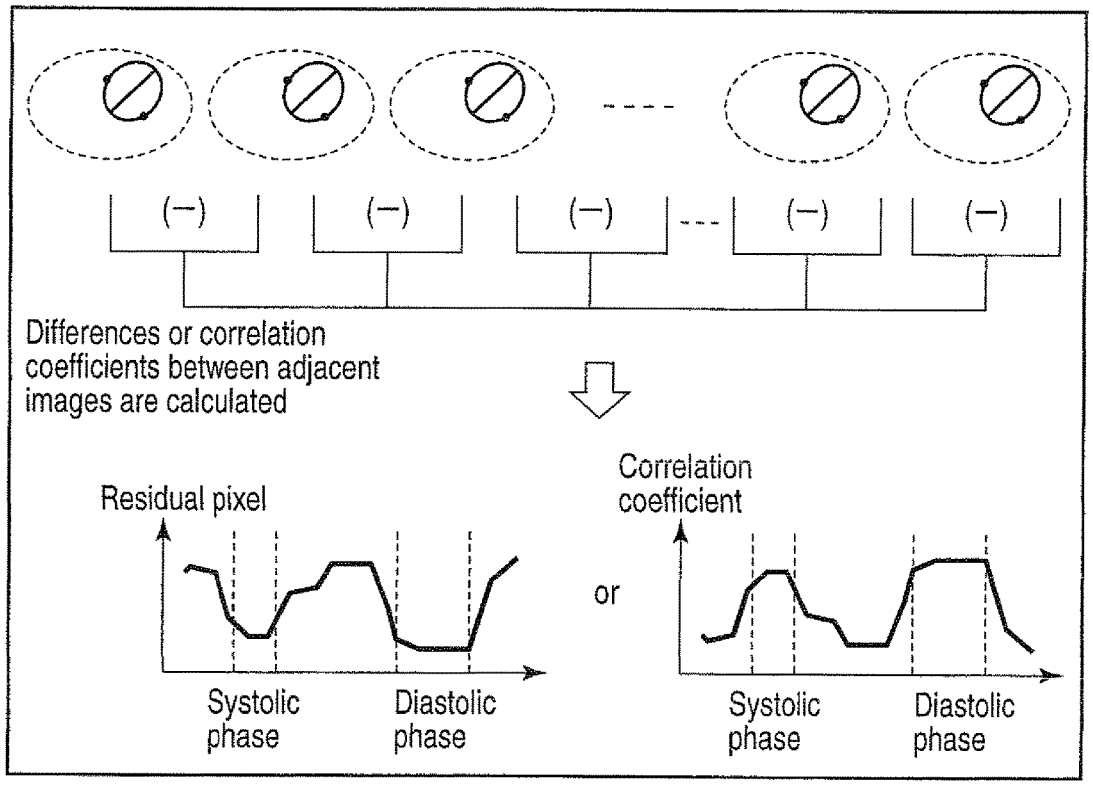
FIG. 10 is a view for explaining correlation coefficient time displacement generation step S14 in FIG. 5.
Figure 11:
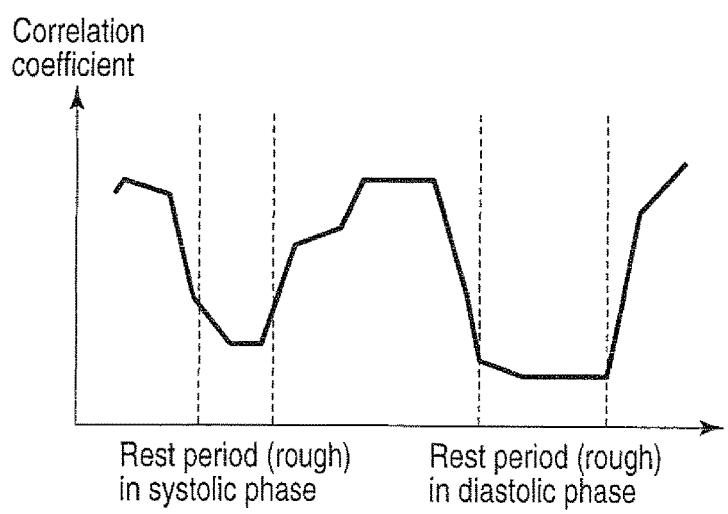
FIG. 11 is a view for explaining rest period determination step S15 in FIG. 5.

A rough rest period determination unit 10*k* determines the first rest period from the obtained temporal change in difference value or correlation coefficient, as shown in FIGS. 10 and 11 (S15). If the difference method is used as this method, a period to be specified as a rest period is a period during which the residual pixel count is lower than a given threshold, and a portion exhibiting little temporal changes continues. If the correlation coefficient method is used as the above method, a period to be specified as a rest period is a period during which the correlation coefficient is higher than a given threshold, and a portion exhibiting little temporal changes continues. The first rest period is typically specified in each of systolic and diastolic phases.

An algorithm for roughly obtaining systolic and diastolic phases by searching an entire cardiac phase assigns, as diastolic and systolic phases, periods in which signal changes become equal to or less than a given range, in descending order of duration (up to n=2).

Figure 9:
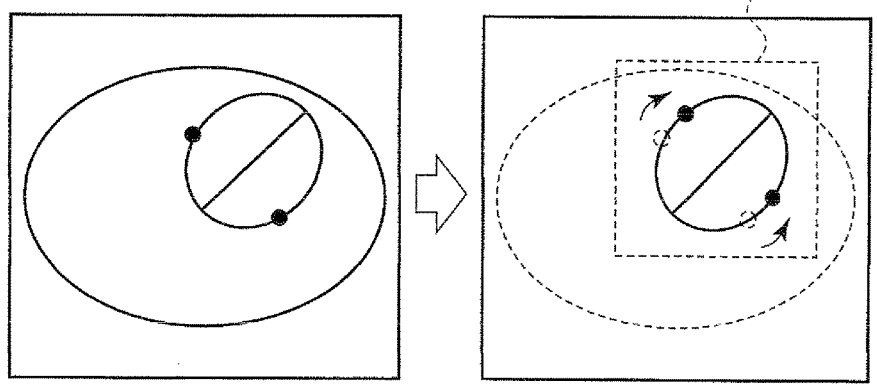
FIG. 9 is a view for explaining correlation coefficient calculation step S13 in FIG. 5.

The method which calculates differences or correlation coefficients between entire images reliably extracts the signal of only a moving portion and leaves it to remain there. On the other hand, the signal of a still portion only remains 0, and the still portion as a calculation target region still remains as the original image region. For this reason, using the correlation coefficient method robust against noise components without any change will require an enormous amount of calculation. As shown in FIG. 9, therefore, the motion index calculation unit 10*j* uses a method of limiting a calculation region by searching for a heart portion by template matching or texture mapping and setting an ROI as a calculation region so as to include the overall heart. This method can reduce the amount of calculation even with the use of the correlation coefficient method.

This apparatus roughly determines rest phases throughout an entire cardiac phase by using the global method as follows: 1) extracting only a moving portion (removing a still portion) upon improving the sensitivity for motions, 2) removing background noise (low signal portions) by threshold processing 1 upon removing noise components due to blood and the like, 3) removing blood portions (high signal portions) by threshold processing 2, and 4) performing difference calculation or crosscorrelation and then reducing the amount of crosscorrelation calculation (performing crosscorrelation upon extracting only a moving portion and extracting only a heart portion by template matching or the like).

The apparatus then uses the local method capable of more precise motion analysis, based on the two first rest periods respectively corresponding to systolic and diastolic phases which are roughly obtained by the above global method. Since the first rest periods obtained by the global method cannot be regarded as accurate because of noise components and the like, the apparatus uses the local method capable of more precise motion analysis. A processing target period for this local method is limited by using the first rest periods obtained by the global method. For this purpose, first of all, a rest period enlargement processing unit 10*m* slightly enlarges the first rest periods roughly obtained by the global method (S16). More specifically, in the enlargement method, the rest period enlargement processing unit 10*m* executes analysis using the local method based on a cine image preceding, by a predetermined time, the time at which the coronary arteries start to come to rest. In practice, it is possible to enlarge each first rest period forward and backward by a predetermined time width or enlarge each first rest period by a predetermined ratio exceeding 1.0.

Note that it is possible to set a period identical to the first rest period as an application range of the local method without enlarging first rest period. The following description is based on the assumption that an enlarged rest period is set as an application range of the local method.

In the local method, first of all, as shown in FIG. 12, an ROI setting unit 10*n* initially sets a local region (ROI) on the first slice image in the enlarged first rest period by using, for example, a template for the right coronary artery in a systolic phase (S17). The apparatus then sequentially searches for a coronary artery region within a search range on the slice image of the next frame by using this local region (ROI) as a visual field. The apparatus uses the search method of calculating the correlation coefficients between a local image portion in the ROI on the immediately preceding frame and a local image portion in the ROI on the next frame and identifying the position of the ROI which exhibits the highest correlation coefficient in the search range as the position of the coronary artery region on the next frame. In this manner, the apparatus sequentially tracks the position of the coronary artery on the slice image in the enlarged first rest period (S18). The same processing as described above is performed to track the left coronary artery. Note that a template for each coronary artery is used for each diastolic phase. A coronary artery template may be based on the average of a plurality of persons or may be a texture. The apparatus displays ROI marks indicating the candidate positions of the ROIs on the coronary arteries, obtained in this manner, on the display unit 10*e* upon superimposing them on a slice image, thereby presenting them to the operator. If the operator affirms the initial position candidates of the display ROIs (four points including two left points and two right points in a systolic phase and a diastolic phase), he/she presses the button to advance to the next step. Otherwise, the operator manually corrects the initial positions of the ROIs and then presses the button to advance to the next step. In the subsequent processing, an ROI displacement detection unit 10*q* searches for a predetermined search range from the initial position of the ROI and detects the next position of the coronary artery, thereby detecting the moving amount of the position of the coronary artery, i.e., the distance (displacement) between the position of the coronary artery on the initial frame and the position of the coronary artery on each frame. The apparatus sequentially replaces the detected ROI position with the new position of the coronary artery, that is, sequentially tracks the position of the coronary artery, based on the displacement obtained in this manner. In this case, it is possible to replace a reference with a new ROI position for each operation or always use the initial ROI position obtained first as a reference and obtain the position of the coronary artery in a slightly large search range from the initial reference position for each operation. Note that obtaining movement from the initial position for each operation will prevent errors from being accumulated.

That is, this apparatus automatically pops up the window shown in FIG. 12 to display the candidate positions of ROIs upon performing matching using a template (average or the like) or texture for each of the left and right coronary arteries in a systolic phase and a diastolic phase. If the operator checks and affirms the candidate positions, he/she immediately presses the continue button to start processing based on the local method. If the operator determines the necessity to correct the positions, he/she corrects them and presses the continue button to start processing based on the local method.

With this displacement detection, a fine rest period determination unit 10p generates temporal changes (time curves) of motion indices indicating variations in the four positions of the left and right coronary arteries like those shown at the bottom of FIG. 12 (S19). The fine rest period determination unit 10p accurately determines rest periods (second rest periods) in states in which the variations of the coronary arteries correspond to small moving amounts so as to fall within predetermined ranges (rest states), from the temporal changes of the motion indices indicating the variations in the four positions of the left and right coronary arteries (S20). Since a rest period needs to be a period during which the movement of the overall coronary arteries is small, the final second rest period is set by ANDing the rest periods of the left and right coronary arteries.

Figure 14:
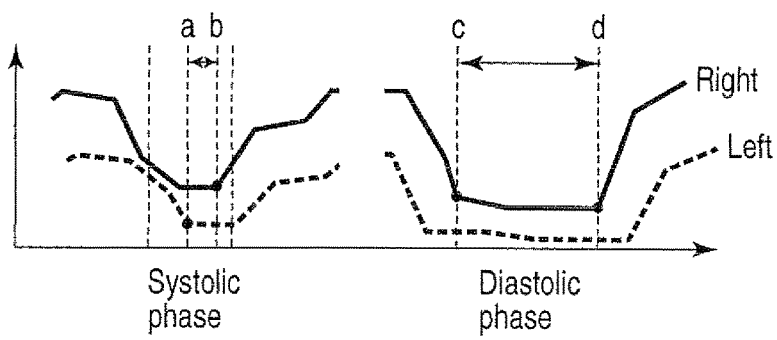
FIG. 14 is a view for explaining rest period determination step S20 in FIG. 5.

That is, as shown in FIG. 14, this apparatus sets latest timings (indicated by "a" in FIG. 14 in a systolic phase, and by "c" in FIG. 14 in a diastolic phase) as the times at which the coronary artery starts to come to rest, and earliest timings (indicated by "b" in FIG. 14 in a systolic phase, and by "d" in FIG. 14 in a diastolic phase) as the times at which the coronary artery starts to move. That is, the apparatus specifies periods during which the displacements of the coronary arteries are equal to or less than predetermined thresholds, as second rest period candidates associated with the left and right coronary arteries, from the temporal changes in the displacements of the four positions of the left and right coronary arteries, and specifies, as the final second rest period, a period in which the second rest period candidates associated with the left and right coronary arteries overlap.

Note that it is possible to separately determine the second rest period corresponding to a systolic phase of the heart and the second rest period corresponding to a diastolic phase of the heart, and to selectively use application ranges of the local method for a systolic phase and diastolic phase of the heart.

In this manner, the temporal changes of motion indices indicating variations in four positions of the left and right coronary arteries in a systolic phase and a diastolic phase are obtained. In order to obtain an image with the highest image quality, periods during which the movement of the coronary arteries is smallest are set as follows. Latest timings (indicated by "a" in FIG. 14 in a systolic phase, and by "c" in FIG. 14 in a diastolic phase) are set as the times at which the coronary artery starts to come to rest, and earliest timings (indicated by "b" in FIG. 14 in a systolic phase, and by "d" in FIG. 14 in a diastolic phase) are set as the times at which the coronary artery starts to move (rest periods are ANDed).

Using this method makes it possible to obtain a rest period of the movement of the overall heart, which is a merit of the global method, while taking advantage of the accurate motion detection performance of the local method.

The WHMR imaging control unit 10r executes a main scan to collect MR data acquired in the second rest periods. The reconstruction unit 10c then reconstructs an image based on the collected data set.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A magnetic resonance (MR) imaging apparatus comprising:

gradient magnetic field generators, at least one radio frequency (RF) coil coupled to an imaging volume, transmitting and receiving units for the at least one RF coil, and a computer system connected to control said gradient magnetic field generators and said RF coil to acquire and process MR signals from patient tissue disposed in said imaging volume, said computer system being configured to repeat an MR imaging scan on an overall heart of a patient, detect displacement of a patient diaphragm due to respiratory movement of the patient by executing an MR probe scan immediately before each of the MR imaging scans, displace an imaging range for each of the MR imaging scans based on the detected displacement of the diaphragm, before each said MR probe scan, generate a series of slice images by executing a preliminary MR scan which repeatedly images a region including the heart using electrocardiogram (ECG) gating, specify, for the series of slice images, a first rest period in which a variation in position of a coronary artery falls within a predetermined range in a cardiac cycle, based on a change in the MR image of the overall heart, specify a second rest period of the coronary artery in the cardiac cycle, after specifying the first rest period, by tracking movement of the coronary artery only within a local range including the coronary artery for a plurality of slice images of the series of slice images, wherein the plurality of slice images corresponds to the first rest period or a rest period enlarged from the first rest period, and the second rest period is included in the first rest period or the rest period enlarged from the first rest period, and reconstruct an image based on MR data acquired using said MR imaging scan in the second rest period.

2. The apparatus according to claim 1, wherein the computer system is further configured to remove a still portion from the series of slice images.

3. The apparatus according to claim 2, wherein the computer system is further configured to Fourier-transform a temporal change in pixel value of each pixel of the series of slice images and remove a pixel exhibiting a frequency not more than a predetermined frequency as the still portion.

4. The apparatus according to claim 2, wherein the computer system is further configured to determine, based on a spatial change in difference between a maximum pixel value and a minimum pixel value in a predetermined period, whether each pixel of the series of slice images is the still portion.

5. The apparatus according to claim 1, wherein the computer system is further configured to specify the first rest period based on a difference result between adjacent frames of the series of slice images.

6. The apparatus according to claim 1, wherein the computer system is further configured to specify the first rest period based on a correlation coefficient between adjacent frames of the series of slice images.

7. The apparatus according to claim 5, wherein the computer system is further configured to calculate the difference result only within a local region including the overall heart.

8. The apparatus according to claim 6, wherein the computer system is further configured to calculate the correlation coefficient only within a local region including the overall heart.

9. The apparatus according to claim 1, wherein the computer system is further configured to enlarge the specified first rest period forward and backward by a predetermined time width.

10. The apparatus according to claim 1, wherein the computer system is further configured to set the local range on each of a left coronary artery and a right coronary artery.

11. The apparatus according to claim 10, wherein the computer system is further configured to set a local range for the left coronary artery and a local range for the right coronary artery by using templates in which a local range for the left coronary artery and a local range for the right coronary artery on slices traversing the heart are respectively set at initial positions.

12. The apparatus according to claim 10, wherein the computer system is further configured to specify the second rest period based on a time curve associated with an index indicating a variation in position of the left coronary artery and a time curve associated with an index indicating a variation in position of the right coronary artery.

13. The apparatus according to claim 10, wherein the computer system is further configured to specify, as the second rest period, a period in which a second rest period candidate obtained from a time curve associated with an index indicating a variation in position of the left coronary artery overlaps a second rest period candidate obtained from a time curve associated with an index indicating a variation in position of the right coronary artery.

14. The apparatus according to claim 10, wherein the computer system is further configured to specify, as the second rest period, one of a second rest period candidate obtained from a time curve associated with an index indicating a variation in position of the left coronary artery and a second rest period candidate obtained from a time curve associated with an index indicating a variation in position of the right coronary artery.

15. The apparatus according to claim 10, wherein the computer system is further configured to determine the second rest period corresponding to each of a systolic phase and diastolic phase of the heart.

16. The apparatus according to claim 1, wherein the computer system is further configured to identify a moving position of the coronary artery from a correlation coefficient of a pixel distribution in the local range between adjacent frames of the slice images.

17. A magnetic resonance (MR) imaging apparatus comprising:
gradient magnetic field generators, at least one radio frequency (RF) coil coupled to an imaging volume, transmitting and receiving units for the at least one RF coil, and a computer system connected to control said gradient magnetic field generators and said RF coil to acquire and process MR signals from patient tissue disposed in said imaging volume, said computer system being configured to
repeat an MR imaging scan on a first organ of a patient,
detect displacement of a second organ of the patient by executing a MR probe scan immediately before each of the MR imaging scans,
displace an imaging range for each of the MR imaging scans based on the detected displacement of the second organ,
before each said MR probe scan, generate a series of slice images by executing a preliminary MR scan which repeatedly images a region including the first organ using electrocardiogram (ECG) gating,
specify a first rest period in which a variation in position of the second organ falls within a predetermined range in a cardiac cycle, by using the series of slice images,
specify, after specifying the first rest period, a second rest period of the second organ by tracking movement of the second organ only within a local range including the second organ for a plurality of slice images of the series of slice images, wherein the plurality of slice images corresponds to the first rest period or a rest period enlarged from the first rest period, and the second rest period is included in the first rest period or the rest period enlarged from the first rest period, and
reconstruct an image based on MR data acquired using said MR imaging scan in the second rest period.

18. An image processing apparatus comprising:
a data storage configured to store data of a series of slice images of a region including a target region of a patient, the series of slice images being acquired by a preliminary magnetic resonance (MR) scan executed in a MR imaging apparatus;
a computer system connected to said data storage to access data within said data storage and configured to:
specify a first rest period based on a change in the region between images of the series of slice images;
specify, after specifying the first rest period, a second rest period shorter than the first rest period by tracking only the target region on a plurality of said slice images corresponding to the specified first rest period or a rest period enlarged from the first rest period, and the second rest period is included in the first rest period or the rest period enlarged from the first rest period; and
control the MR imaging apparatus to perform a main MR scan of the target region during the second rest period to acquire MR data.

* * * * *